(12) United States Patent
Schwendner et al.

(10) Patent No.: US 6,355,628 B1
(45) Date of Patent: Mar. 12, 2002

(54) COMBINATION THERAPY USING PENTAFLUOROBENZENESULFONAMIDES

(75) Inventors: Susan Schwendner, San Bruno; Pieter Timmermans, Redwood City; Jacqueline Walling, Burlingame, all of CA (US)

(73) Assignee: Tularik Inc., So. San Francisco, CA (US)

( * ) Notice: Subject to any disclaimer, the term of this patent is extended or adjusted under 35 U.S.C. 154(b) by 0 days.

(21) Appl. No.: 09/627,041

(22) Filed: Jul. 27, 2000

Related U.S. Application Data
(60) Provisional application No. 60/146,436, filed on Jul. 29, 1999.

(51) Int. Cl.[7] .................. A61K 31/66; A61K 31/415; A61K 31/34; A61K 31/28
(52) U.S. Cl. .................. 514/117; 514/406; 514/471; 514/479; 514/492
(58) Field of Search .................. 514/117, 406, 514/471, 479, 492

(56) References Cited

U.S. PATENT DOCUMENTS

| | | | |
|---|---|---|---|
| 1,955,207 A | 4/1934 | Stotter et al. | 167/37 |
| 2,402,623 A | 6/1946 | Hester et al. | 260/556 |
| 3,034,955 A | 5/1962 | Frick et al. | 167/37 |
| 4,881,969 A | 11/1989 | Saupe et al. | 71/94 |
| 4,883,914 A | 11/1989 | Alvarado et al. | 564/91 |
| 4,900,867 A | 2/1990 | Wilkes et al. | 564/91 |
| 5,250,549 A | 10/1993 | Yoshino et al. | 514/345 |
| 5,385,931 A | 1/1995 | Bigg et al. | 514/443 |
| 5,387,709 A | 2/1995 | Lardy et al. | 558/388 |
| 5,773,236 A | 6/1998 | Diwu et al. | 435/15 |
| 5,880,151 A | 3/1999 | Medina et al. | 514/518 |
| 5,891,917 A | 4/1999 | Tange et al. | 514/604 |

FOREIGN PATENT DOCUMENTS

| | | |
|---|---|---|
| EP | 0 469 901 A1 | 2/1992 |
| EP | WO 97/30677 | 4/1994 |
| GB | 1242057 | 8/1971 |
| GB | 1306564 | 2/1973 |

OTHER PUBLICATIONS

Fielding, et al.; "Synthesis and reactions of 4-sulpho-2,3,5,6,-tetrafluorobenzoic acid", *Journal of Fluorine Chemistry*, Oct. 1992, Vol. 59, No. 1, pp. 15–31.

Raibekas, et al.; "Affinity Probing of Flavin Binding Sites. 2. Identification of a Reactive Cysteine in the Flavin Domain of *Escherichia coli* DNA Photolyase"; *Biochemistry* 1994, vol. 33, No. 42, pp. 12656–12664.

Shealy, et al.; "2–Haloethylating Agents for Cancer Chemotherapy. 2–Haloethyl Sulfonates"; *Journal of Medicinal Chemistry*, Aug. 1983, vol. 26, No. 8, pp. 1168–1173.

Olander, et al.; "A Study of the Binding of Two Sulfonamides to Carbonic Anhydrase"; *Journal of the American Chemical Society*, Mar. 1973, vol. 95, No. 5, pp. 1616–1621.

Hawkinson, et al.; "Studies of the Solvolysis of 2–Adamantyl Pentafluorobenzenesulfonate: A $Y_{PFBS}$ Scale[1]"; *The Journal of Organic Chemistry*, Aug., 1988, vol. 53, No. 16, pp. 3857–3860.

Bai, et al.; "Identification of the Cysteine Residue of β–Tubulin Alkylated by the Antimitotic Agent 2,4–Dichlorobenzyl Thiocyanate, Facilitated by Separation of the Protein Subunits of Tubulin by Hydrophobic Column Chromatography"; *Biochemisty* 1989, vol. 28, pp. 5606–5612.

Fadeeva, V.P., "Gas–chromatography separation of sulfur–and fluorine–containing pyrolysis products", *Chemical Abstracts*, 76:(5) (Jan. 31, 1972).

Gerig et al., "Aromatic Rign Dynamics in a Carbonic Anhydrase–Inhibitor Complex", *Journal of the Chemical Society Chemical Communications*, No. 6, pp 482–484 (1987).

Luduena, E.F., et al. Interaction of Ethacrynic Acid with Bovine Brain Tubulin, *Biochemical Pharmacology*, 47:(9) 1677–1681 (Apr. 29, 1994).

March, Advanced Organic Chemistry, 4th Edition, 1992 p. 497.

Yoshimoto et al., "Correlation Analysis of Baker's Studios . . . ", J. Med. Chem, 19:(1) 71–98 (1976).

*Primary Examiner*—Peter O'Sullivan
(74) *Attorney, Agent, or Firm*—Townsend and Townsend and Crew LLP

(57) ABSTRACT

Combination therapies are provided for the treatment of proliferative disorders which use a pentafluorobenzenesulfonamide of formula I and an antineoplastic platinum coordination complex such as cisplatin.

12 Claims, 5 Drawing Sheets

ARROW INDICATES DOSE ADMINISTRATION (DAY 1). RESULTS ARE EXPRESSED AS THE MEAN ± SEM

ARROW INDICATES DOSE ADMINISTRATION (DAY 1). RESULTS ARE EXPRESSED AS THE MEAN ± SEM

COMPOUND 1
(SODIUM SALT)

COMPOUND 2

COMPOUND 3

COMBINATION THERAPY USING PENTAFLUOROBENZENESULFONAMIDES

CROSS-REFERENCES TO RELATED APPLICATIONS

This Application claims priority to U.S. patent application Ser. No. 60/146,436, filed Jul. 29, 1999, the disclosure of which is incorporated by reference.

STATEMENT AS TO RIGHTS TO INVENTIONS MADE UNDER FEDERALLY SPONSORED RESEARCH AND DEVELOPMENT

Not applicable

BACKGROUND OF THE INVENTION

FIELD OF THE INVENTION

The present invention relates to combinations of pentafluorobenzenesulfonamides and cisplatin that are capable of inhibiting abnormal cell proliferation.

BACKGROUND

Cancer is a generic name for a wide range of cellular malignancies characterized by unregulated growth, lack of differentiation, and the ability to invade local tissues and metastasize. These neoplastic malignancies affect, with various degrees of prevalence, every tissue and organ in the body. A multitude of therapeutic agents have been developed over the past few decades for the treatment of various types of cancer. The most commonly used types of anticancer agents include: DNA-alkylating agents (e.g., cyclophosphamide, ifosfamide), antimetabolites (e.g., methotrexate, a folate antagonist, and 5-fluorouracil, a pyrimidine antagonist), microtubule disrupters (e.g., vincristine, vinblastine, paclitaxel), DNA intercalators (e.g., doxorubicin, daunomycin, cisplatin), and hormone therapy (e.g., tamoxifen, flutamide). The ideal antineoplastic drug would kill cancer cells selectively, with a wide therapeutic index relative to its toxicity towards non-malignant cells. It would also retain its efficacy against malignant cells, even after prolonged exposure to the drug. Unfortunately, none of the current chemotherapies possess an ideal profile. Most possess very narrow therapeutic indexes and, in practically every instance, cancerous cells exposed to slightly sublethal concentrations of a chemotherapeutic agent will develop resistance to such an agent, and quite often cross-resistance to several other antineoplastic agents.

The development of new anticancer agents has given rise to new treatment regimens and new combinations that are proving more effective in combating this disease.

Accordingly, it is one object of the present invention to provide compositions which directly or indirectly are toxic to actively dividing cells and are useful in the treatment of cancer.

A further object of the present invention is to provide methods for killing actively proliferating cells, such as cancerous, bacterial, or epithelial cells, and treating all types of cancers, and generally proliferative conditions. A further object is to provide methods for treating other medical conditions characterized by the presence of rapidly proliferating cells, such as psoriasis and other skin disorders.

Additional objects, features and advantages will become apparent to those skilled in the art from the following description and claims.

SUMMARY OF THE INVENTION

In one aspect, the present invention provides compositions useful for the treatment of cancer and other diseases associated with abnormal cell proliferation. The compositions comprise cisplatin (or a related platinum coordination complex, e.g., carboplatin) and a compound having the formula:

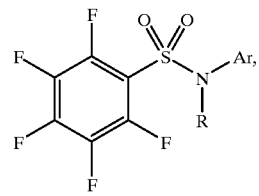

(I)

In the formula above, the letter R represents a hydrogen, substituted or unsubstituted ($C_1$–$C_{10}$)alkyl, or substituted or unsubstituted ($C_3$–$C_6$)alkenyl. The symbol Ar represents a substituted or unsubstituted aryl group or a substituted or unsubstituted heteroaryl group.

In another aspect, the present invention provides methods for the treatment of cancer and other proliferative disorders using the compositions provided above.

DESCRIPTION OF THE SPECIFIC EMBODIMENTS

Definitions

Figure 1:
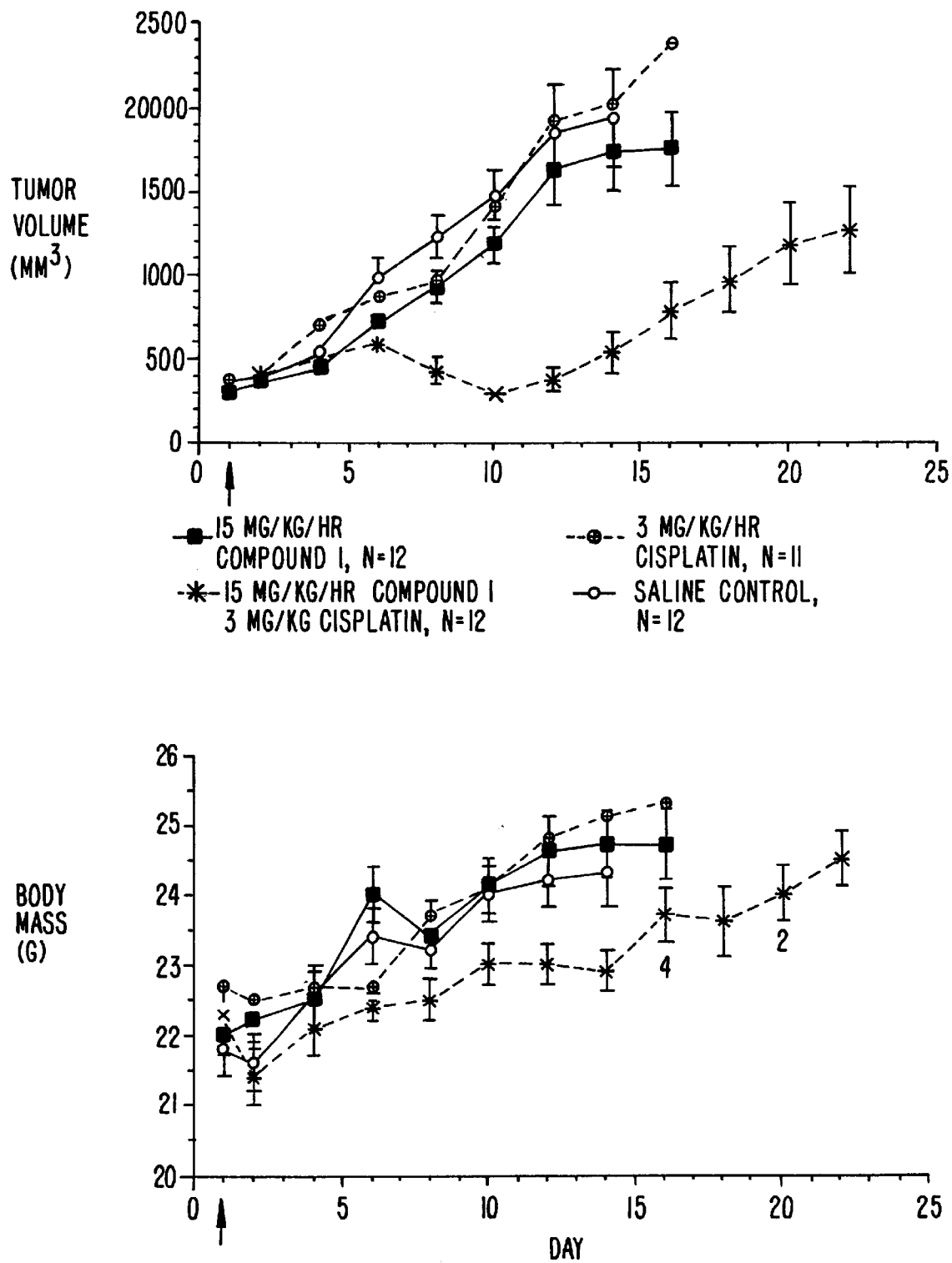
FIG. 1 is a graph which illustrates the synergistic effects of Compound 1 with cisplatin in the treatment of MX-1 human mammary tumor xenografts in athymic nude mice, using suboptimal doses of each of the agents.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$–$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl." Alkyl groups which are limited to hydrocarbon groups are termed "homoalkyl".

The term "alkylene" by itself or as part of another substituent means a divalent radical derived from an alkane, as exemplified by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quatemized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH═CH—O—$CH_3$, —Si($CH_3$)$_3$, —$CH_2$—CH═N—O$CH_3$, and —CH═CH—N($CH_3$)—$CH_3$. Up to two heteroatoms may be consecutive, such as, for example, —$CH_2$—NH—O$CH_3$ and —$CH_2$—O—Si($CH_3$)$_3$. Similarly, the term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2, 5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo ($C_1$–$C_4$)alkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quatemized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', ═O, ═NR', ═N—OR', —NR'R", —SR', -halogen, —SiR'R"R'", —OC(O)R', —C(O)R', —CO$_2$R', —CONR"R", —OC(O)NR'R", —NR"C(O)R', —NR'—C(O)NR"R'", —NR"C(O)$_2$R', —NH—C(NH$_2$)═NH, —NR'C(NH$_2$)═NH, —NH—C(NH$_2$)═NR', —S(O)R', —S(O)$_2$R', —S(O)$_2$NR"R", —CN and —NO$_2$ in a number ranging from zero to (2 m'+1), where m' is the total number of carbon atoms in such radical. R', R" and R'" each independently refer to hydrogen, unsubstituted ($C_1$–$C_8$)alkyl and heteroalkyl, unsubstituted aryl, aryl substituted with 1–3 halogens, unsubstituted alkyl, alkoxy or thioalkoxy groups, or aryl-($C_1$–$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)

=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R" and R'" are independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl) oxy-(C$_1$-C$_4$)alkyl.

Two of the substituents on adjacent atoms of the aryl or heteroaryl ring may optionally be replaced with a substituent of the formula —T—C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula —A—(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic finctionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

General

A number of arylsulfonamides have recently been described for the treatment of disorders and conditions arising from abnormal cell proliferation and from elevated plasma cholesterol levels. gee, for example, PCT publications WO 97/30677, WO 98/05315 and WO 99/10320. Representative of this new class of anticancer agents are the pentafluorobenzenesulfonamides described in WO 98/05315. These agents are thought to exert their effect by binding to β-tubulin and disrupting microtubule formation. See, (publication of T-compound activity).

Still other pentafluorobenzenesulfonamides have been described in co-pending applications Ser. Nos. 60/090,681 filed Jun. 25, 1998 and Ser. No. 09/336,062 filed Jun. 18, 1999; Ser. No. 60/093,570 filed Jul. 20, 1998 and Ser. No. 09/353,976 filed Jul. 15, 1999; and Ser. No. 60/100,888 filed Sep. 23, 1998.

Clinical trials are in progress to evaluate the pentafluorobenzenesulfonamide class of compounds for the treatment of cancer.

Cisplatin (cis-diaminedichloroplatinum (II)) is a platinum coordination complex first identified in 1965 as a cytotoxic agent. It has broad activity as an antineoplastic agent and is especially useful in the treatment of epithelial malignancies.

Other platinum coordination complexes that have been evaluated in clinical trials include carboplatin, tetraplatin, ormiplatin, iproplatin and oxaliplatin (see Kelland, *Crit. Rev. Oncol. Hematol.*, 15:191–219 (1993)).

Combinations of cisplatin and a pentafluorobenzenesulfonamide derivative have now been evaluated against tumor xenografts in mice and, quite surprisingly, have been found to provide synergistic levels of activity.

Description of the Embodiments
Compositions

In one aspect, the present invention provides compositions comprising an antineoplastic platinum coordination complex and a compound having the formula:

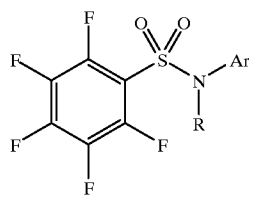

(I)

or a pharmaceutically acceptable salt thereof.

In the formula above, the letter R represents a hydrogen, substituted or unsubstituted $(C_1-C_{10})$alkyl, or substituted or unsubstituted $(C_3-C_6)$alkenyl. The symbol Ar represents a substituted or unsubstituted aryl group or a substituted or unsubstituted heteroaryl group.

In preferred embodiments, R represents a hydrogen or a substituted or unsubstituted $(C_1-C_4)$alkyl group, more preferably hydrogen, methyl or ethyl.

Also preferred are those embodiments in which Ar represents a substituted aryl or substituted heteroaryl group, preferably those having a single ring (e.g., substituted phenyl, substituted pyridyl and substituted pyrimidyl). Particularly preferred embodiments are those in which Ar is substituted phenyl. For those embodiments in which Ar is substituted phenyl, the substituents will typically be present in a number of from one to three. Preferred substituents are selected from -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', perfluoro(C$_1$–C$_4$) alkoxy, and perfluoro(C$_1$–C$_4$)alkyl, where R', R" and R'" are independently selected from hydrogen, $(C_1-C_4)$alkyl, unsubstituted aryl and heteroaryl, (unsubstituted aryl)-$(C_1-C_4)$alkyl, and (unsubstituted aryl)oxy-$(C_1-C_4)$alkyl. Particularly preferred substituents are halogen, $(C_{1-4})$alkyl, —OR', —OC(O)R', —NR'R", —CO$_2$R', —CONR'R", —C(O)R', —OC(O)NR'R", —NR"C(O)R', —NR"C(O)$_2$R', —NR'—C(O)NR"R'", perfluoro(C$_1$–C$_4$)alkoxy, and perfluoro(C$_1$–C$_4$)alkyl, in which R', R" and R'" are hydrogen or $(C_1-C_4)$alkyl. Still further preferred are those embodiments in which Ar is selected from:

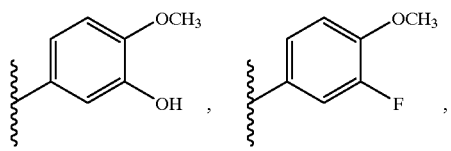

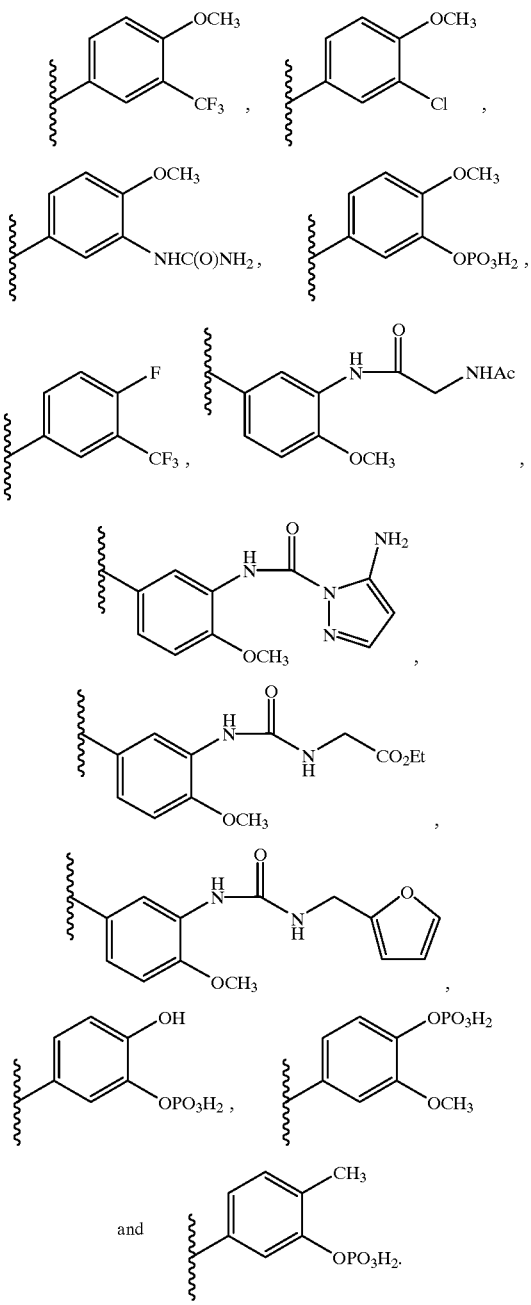

In the most preferred embodiments of the invention, the pentafluorobenzenesulfonamide compound used in the composition is selected from:

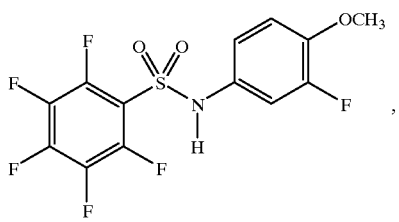

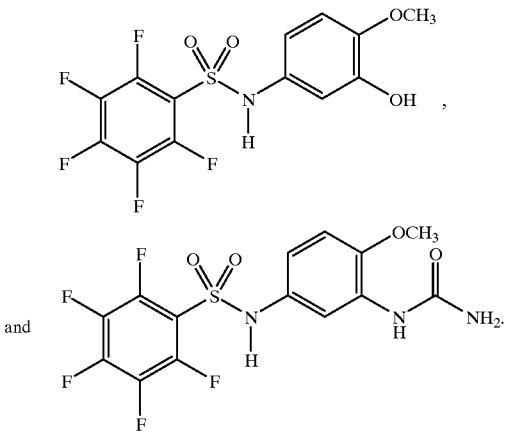

The compositions of the present invention will further comprise an antineoplastic platinum coordination complex. Examples of such complexes include cisplatin, carboplatin, tetraplatin, ormiplatin, iproplatin, oxaliplatin and the like. Preferably, the platinum coordination complex will be cisplatin or carboplatin, more preferably cisplatin.

Methods of Treating Proliferative Disorders

The present invention provides, in another aspect, methods for the treatment of proliferative disorders. In one embodiment, treatment is carried out using a composition comprising each of the two agents described above. In another embodiment, treatment comprises separate administration of an antineoplastic platinum coordination complex and a pentafluorophenylsulfonamide of formula I.

i. Combination Composition

In this embodiment of the invention, a composition of two agents (described above) is administered to a patient in need of treatment. The amount of each agent will typically be less than an amount that would produce a therapeutic effect if administered alone. The precise method of administration will depend on the patient and the judgment of the clinician, but will preferably be intravenous.

ii. Compositions Used Sequentially (administer each separately)

In this embodiment of the invention, conventional protocols are described for the administration of cisplatin (as representative of the antineoplastic platinum coordination complexes) and compound 1 (as representative of the compounds of formula I). One of skill in the art will understand that various changes can be made by the clinician, depending on the particular agents selected for use and the routes and timing of administration.

The cisplatin is preferably administered with a single intravenous infusion on day one of compound 1 administration period about four hours after the first day's administration of compound 1. To maintain sufficient hydration, one liter of normal saline with 20 meq KCl/L and 1 gm of magnesium sulfate, at a rate of about 250 ml/hour is administered prior to and after the cisplatin infusion. The amount of cisplatin in the infusion is preferably 25 to 300 mg per $m^2$ of the patient's body surface area, more preferably 50 to 150 mg/$m^2$ and most preferably 75 to 100 mg/$m^2$. Additional fluid may be given to maintain adequate urine output. The cisplatin is preferably administered with 500 ml of normal saline containing 12.5 gm mannitol over a one hour period. Alternatively the a dosage of cisplatin listed in the above paragraph could be administered over a 2 to 5 day period. Up to 100 mg/day/$m^2$ of patent's body surface area could be administered daily for 5 consecutive days.

After a period of about 28 to 42 days, preferably 28 days, from the first day of the compound 1 administration period, another administration cycle may be performed, with compound 1 being administered on day one and on each subsequent day of the administration period and cisplatin being administered on day one, or less preferably over a period of 2 to 5 days. For example, for a five-day compound 1 administration period, a one-day cisplatin administration period, and a 28 day treatment cycle, the treatment will take place for five days (compound 1 treatment on days 1 through 5 and cisplatin treatment on day 1), followed by 28−5=23 days during which no treatment is given, followed by five more days of treatment as the start of the second cycle.

The treatment cycles may be continued until a clinical response is achieved or until intolerable side effects are encountered. The dosages of compound 1 . and/or cisplatin may be increased with each new treatment cycle, provided intolerable side effects are not encountered. The dosages may also be decreased, if intolerable side effects are encountered. It is presently preferred to gradually adjust the dosage of compound 1 while holding the cisplatin dosage constant.

A common, but tolerable side effect of cisplatin is nausea and vomiting. This can be alleviated by administering an anti-emetic (e.g., Ondansetron, Granisetron, Decadron, Haldol, Benadryl, Ativan and the like).

Of course, other forms of administration of both active ingredients, as they become available, are contemplated, such as by nasal spray, transdermally, by suppository, by sustained release dosage form, by IV injection, etc. Any form of administration will work so long as the proper dosages are delivered without destroying the active ingredient.

The effectiveness of treatment may be determined by controlled clinical trials. Patients having cancer with measurable or evaluable tumors will be included in the study. A measurable tumor is one that can be measured in at least two dimensions such as a lung tumor surrounded by aerated lung, a skin nodule, or a superficial lymph node. An evaluable tumor in one that can be measured in one dimension such as a lung tumor not completely surrounded by aerated lung or a palpable abdominal or soft tissue mass that can be measured in one dimension. Tumor markers which have been shown to be highly correlated with extent of disease will also be considered to provide an evaluable disease, such as PSA for prostate cancer, CA-125 for ovarian cancer, CA-15-3 for breast cancer, etc.

The tumor will be measured or evaluated before and after treatment by whatever means provides the most accurate measurement, such as CT scan, MRI scan, Ultrasonography, etc. New tumors or the lack thereof in previously irradiated fields can also be used to assess the anti-tumor response. The criteria for evaluating response will be similar to that of the WHO Handbook of Reporting Results of Cancer Treatment, WHO Offset Publication 1979, 49-World Health Organization, Geneva. The following results are defined for uni- and bi-dimensionally measurable tumors.

Complete response: Complete disappearance of all clinically detectable malignant disease determined by two observations not less than four weeks apart.

Partial Response: (a) for bidimensionally measurable tumors, a decrease of at least 50% in the sum of the products of the largest perpendicular diameters of all measurable tumors as determined by two observations not less than four weeks apart. (b) for unidimensionally measurable tumors, a decrease by at least 50% in the sum of the largest diameters of all tumors as determined by two observations not less than four weeks apart. In cases where the patient has multiple tumors, It is not necessary for all tumors to have regressed to achieve a partial response as defined herein, but no tumor should have progressed and no new tumor should appear.

Stable disease: (a) for bidimensionally measurable tumors, less than a 50% decrease to less than a 25% increase in the sum of the products of the largest perpendicular diameters of all measurable tumors. (b) for unidimensionally measurable tumors, less than a 50% decrease to less than a 25% increase in the sum of the diameters of all tumors. For (a) and (b) no new tumors should appear.

No clinical response, i.e. progressive disease in defined as an increase of more than 50% in the product of the largest perpendicular diameters for at least one bidimensionally measurable tumor, or an increase of more than 25% in measurable dimension of at least one unidimensionally measurable tumor.

Of course elimination or alleviation of other known signs or symptoms of cancer, especially those listed previously can also be used to evaluate the effectiveness of this invention.

The cancers should be evaluated, i.e. tumors measured, etc., no more than 14 days before the start of the treatment. These cancers should be reevaluated about 28 days after day 1 of administration of the first dose of compound 1 and cisplatin. Twenty eight days after this initial administration another administration period may be performed, and evaluations performed 28 days after the start of this second cycle. The treatment cycles may be continued until a clinical response is achieved or unacceptable toxicity is encountered.

Another aspect of this invention is the treatment of cancer with reduced side effects normally associated with cisplatin. This objective can be achieved by administration of lower doses of the two active ingredients or by shorter duration of dosing brought about by the synergistic effect of the combination.

The most common side effect of cisplatin is nephrotoxicity. Dose limiting toxicity would cause serum creatinine of more than 2.2 mg/dL persisting for more than 2 weeks from the time of dosing.

EXAMPLES

Example 1

This example illustrates the synergy observed between cisplatin and 2-fluoro-1-methoxy-4-(pentafluorophenylsulfonamido)benzene, sodium salt against MX-1 human mammary tumor xenografts in athymic nude mice.

2-Fluoro-1-methoxy-4-(pentafluorophenylsulfonamido) benzene, sodium salt (Compound 1) prevents tubulin polymerization by covalently binding to β-tubulin and inhibits the growth and clonogenic potential of various tumor cell lines in culture. Its activity is not affected by the multidrug resistance (MDR) phenotype. A dose of 30 mg/kg/hr of compound 1 infused i.v. for 4 hours was found to be very effective at inhibiting the growth of MX-1 human mammary tumor xenografts in athymic nude mice. Cisplatin was also very efficacious against this tumor. The efficacy of both agents was accompanied by body weight loss.

Administration of suboptimal doses of 3 mg/kg cisplatin i.v. bolus or 15 mg/kg/hr compound 1 i.v. infusion for 4 hours was compared with the efficacy of coadministration against MX-1 tumors. The combined administration of compound 1 and cisplatin resulted in a significant enhancement of efficacy compared to the administration of either compound alone (see FIG. 1). This coadministration of suboptimal doses resulted in much less weight loss and mortality than seen when these compounds are administered alone at an efficacious dose. These finding show that administration of a combination of suboptimal doses of compound 1 and cisplatin result in a synergistic inhibition of tumor growth with less drug toxicity.

Figure 2:
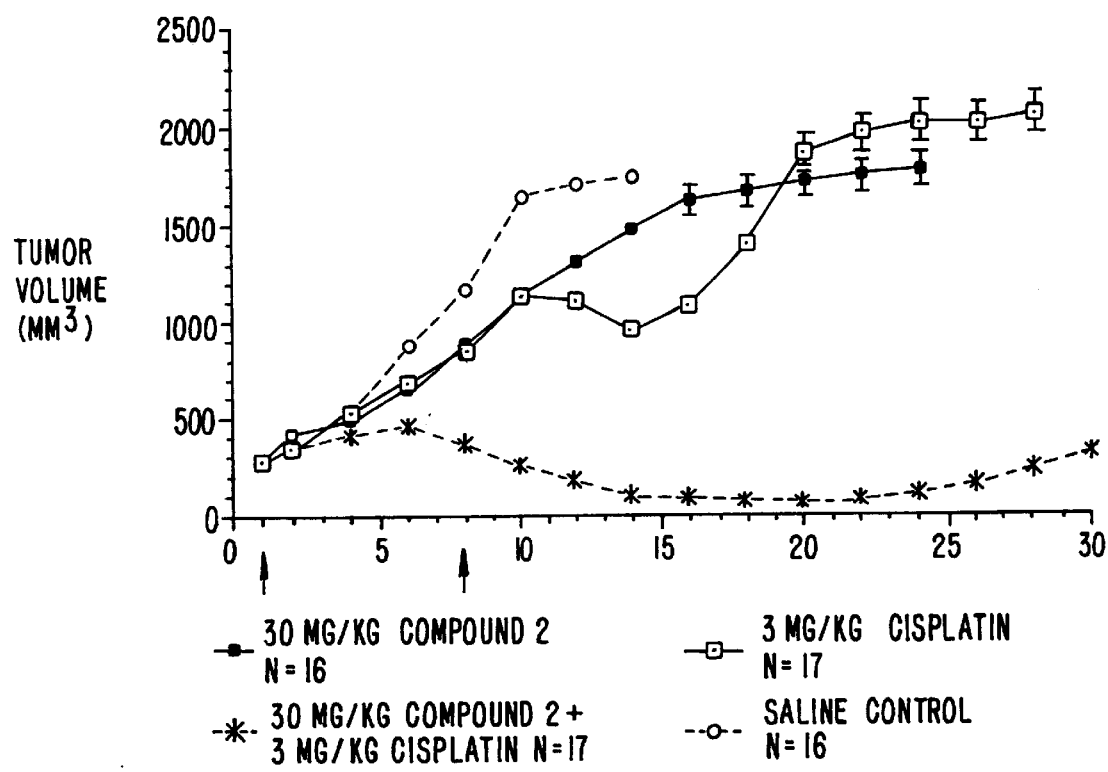
FIG. 2 is a graph which illustrates the synergistic effects of Compound 2 with cisplatin in the treatment of MX-1 human mammary tumor xenografts in athymic nude mice, using suboptimal doses of each of the agents.
Figure 2:
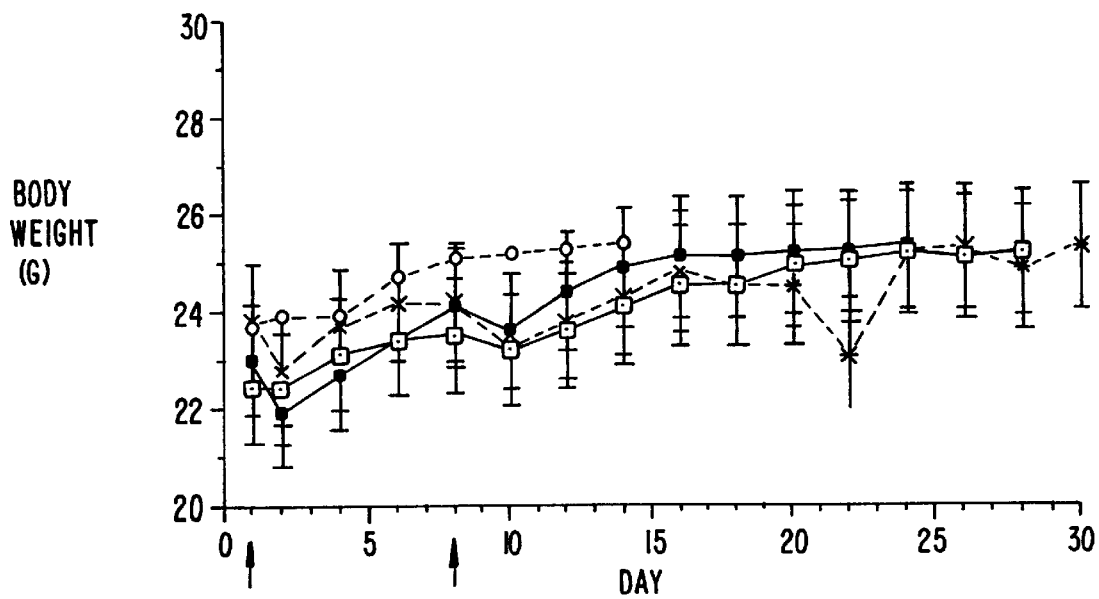
Figure 3:
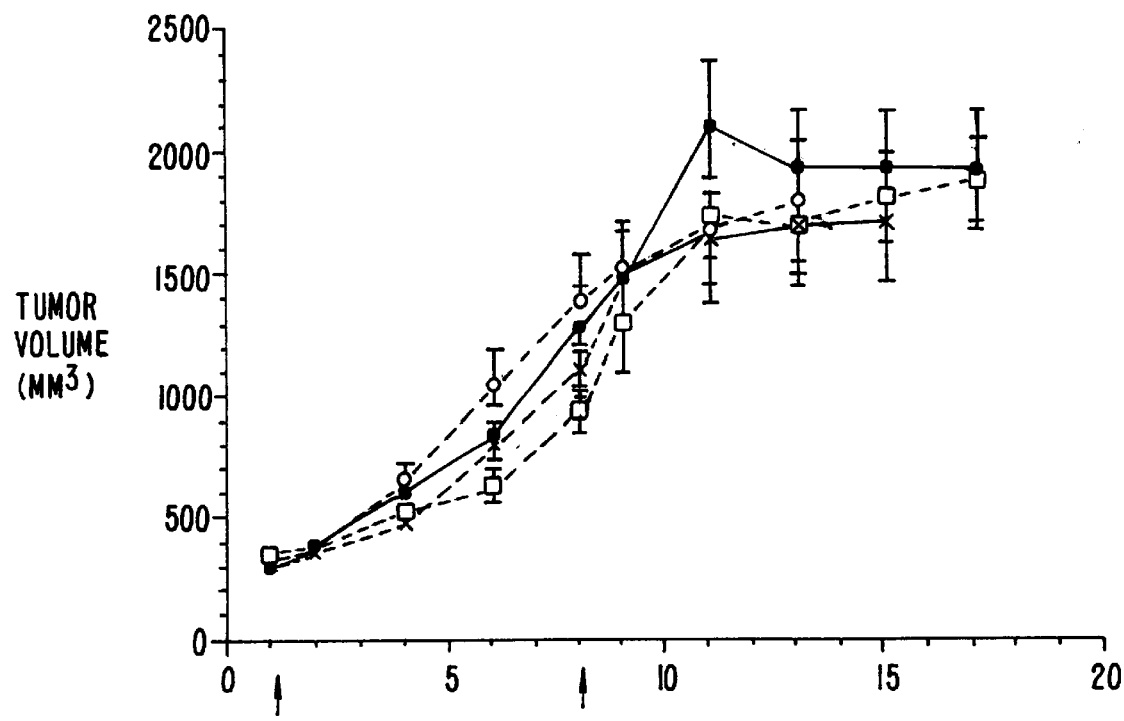
FIG. 3 is a graph which illustrates the lack of synergistic activity between 5-fluorouracil and Compound 2 against MX-1 human mammary tumor xenografts in athymic nude mice.
Figure 3:
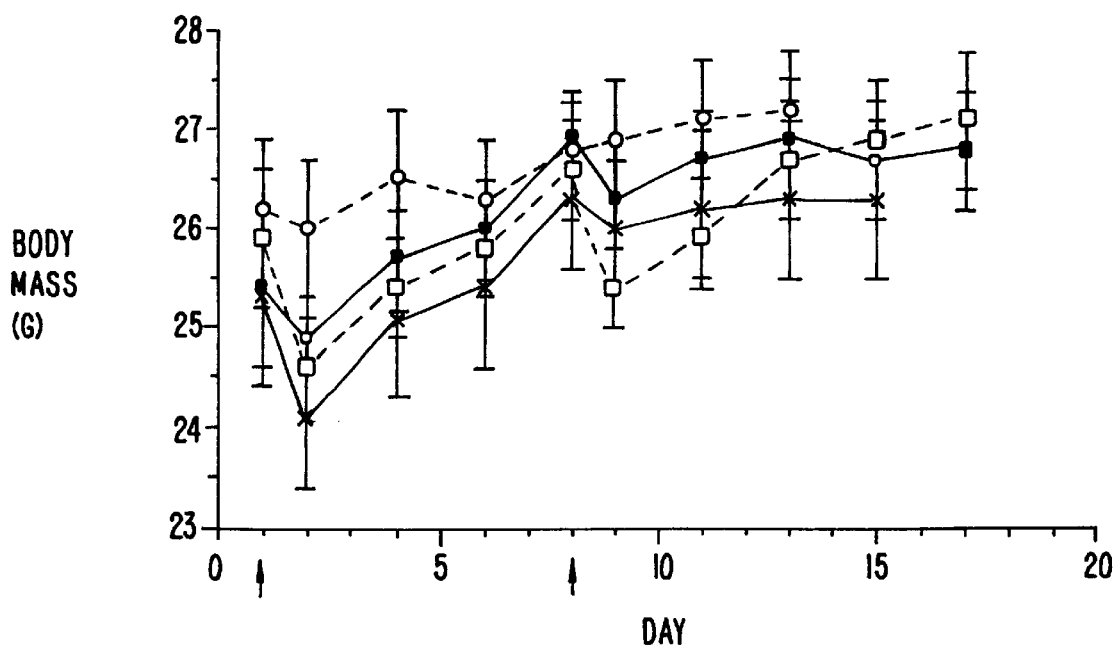
Figure 4:
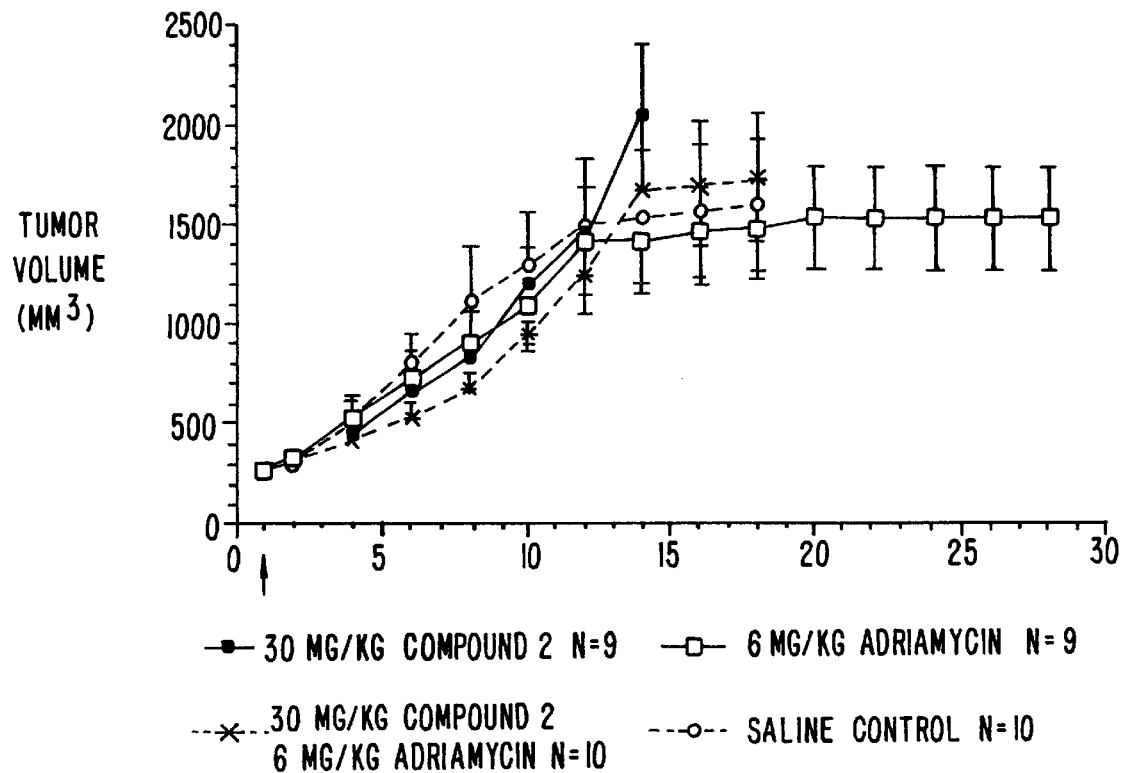
FIG. 4 is a graph which illustrates the lack of synergistic activity between adriamycin and Compound 2 against MX-1 human mammary tumor xenografts in athymic nude mice.
Figure 4:
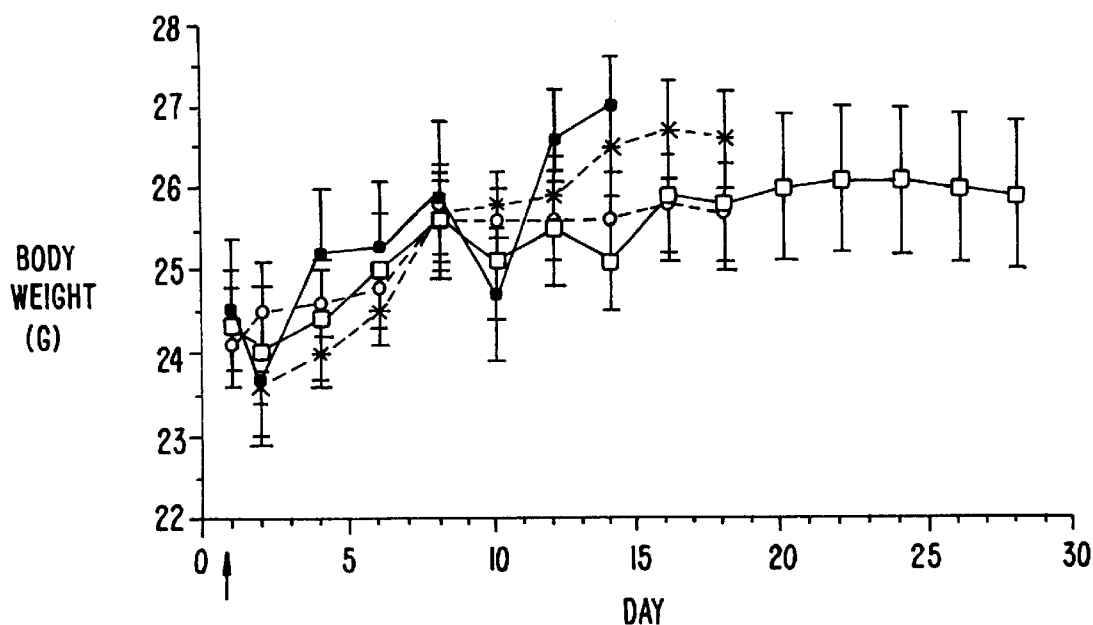
Figure 5:
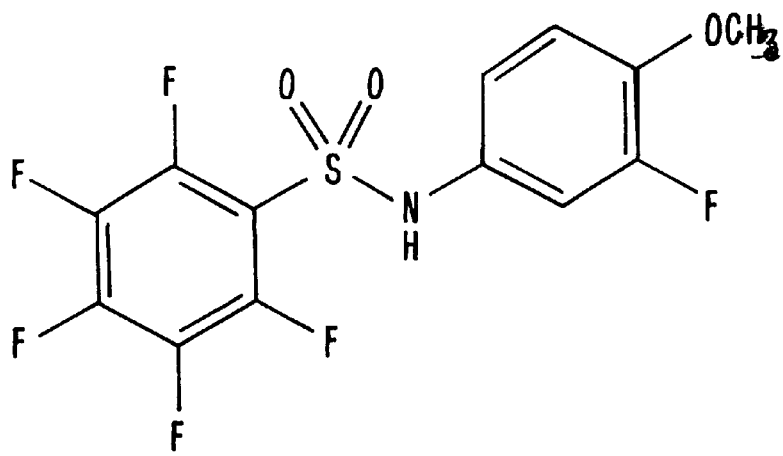
FIG. 5 provides the structures of Compound 1, Compound 2 and Compound 3.
Figure 5:
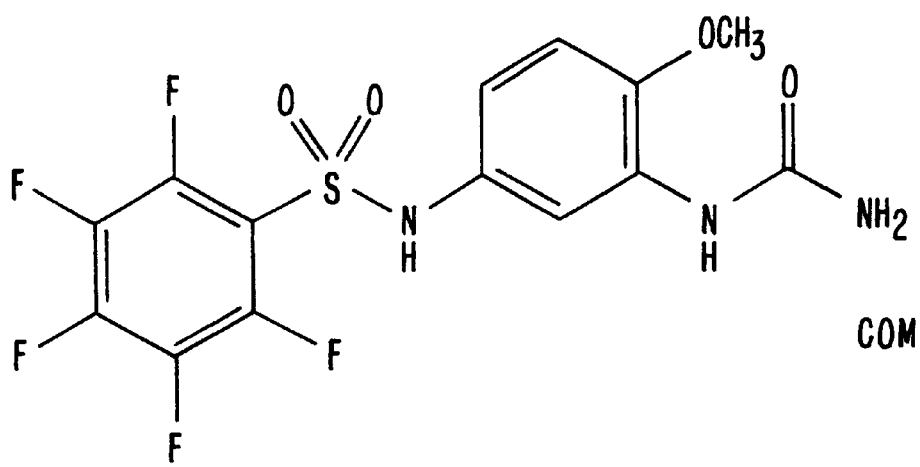
Figure 5:
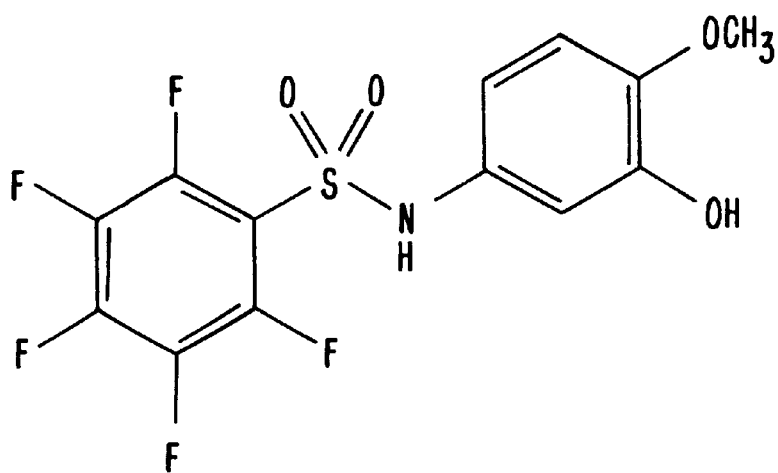

Similar results were obtained for N-(1-methoxy-4-(pentafluorophenylsulfonamido)benzene urea (Compound 2, see FIG. 2). Combinations of compound 2 and either 5-fluorouracil (FIG. 3) or adriamycin (FIG. 4) did not produce similar results.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teaching of this invention that certain changes and modifications may be made thereto without departing from the spirit or scope of the appended claims.

What is claimed is:

1. A composition for the treatment of proliferative disorders, comprising an antineoplastic platinum coordination complex and a compound having the formula:

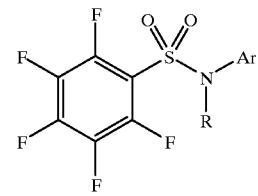

and pharmaceutically acceptable salts thereof;
wherein
R is a member selected from the group consisting of hydrogen and substituted or unsubstituted ($C_1$–$C_{10}$) alkyl; and
Ar is a member selected from the group consisting of substituted or unsubstituted aryl and substituted or unsubstituted heteroaryl.

2. A composition in accordance with claim 1, wherein said antineoplastic platinum coordination complex is selected from the group consisting of cisplatin, carboplatin, tetraplatin, ormiplatin, iproplatin and oxaliplatin.

3. A composition in accordance with claim 1, wherein said antineoplastic platinum coordination complex is cisplatin.

4. A composition in accordance with claim 1, wherein R is hydrogen or unsubstituted ($C_1$–$C_4$)alkyl.

5. A composition in accordance with claim 1, wherein Ar is a substituted phenyl group.

6. A composition in accordance with claim 5, wherein said substituents on said phenyl group are selected from the group consisting of halogen, ($C_1$–$C_4$)alkoxy, ($C_1$–$C_4$)alkyl, and —OPO$_3$H$_2$.

7. A composition in accordance with claim 6, wherein Ar represents a member selected from the group consisting of

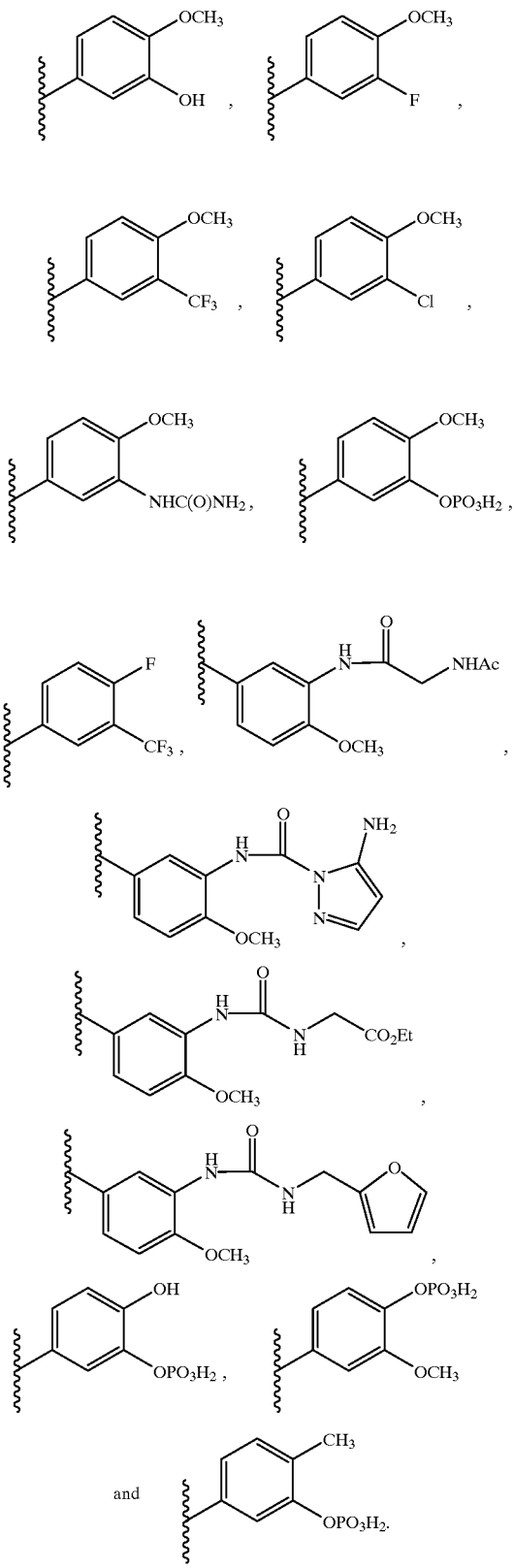

9. A method for the treatment of a proliferative disorder, comprising administering to a subject in need of such treatment an effective amount of a composition of claim 1.

10. A method for the treatment of a proliferative disorder, comprising administering to a subject in need of such treatment:

i) a first amount of an antineoplastic platinum coordination complex; and ii) a second amount of a compound of formula:

and pharmaceutically acceptable salts thereof; wherein

R is a member selected from the group consisting of hydrogen and substituted or unsubstituted ($C_1$–$C_{10}$) alkyl; and Ar is a member selected from the group consisting of substituted or unsubstituted aryl and substituted or unsubstituted heteroaryl;

wherein said first amount and said second amount, in combination, are effective to treat said proliferative disorder.

11. A method in accordance with claim 10, wherein said antineoplastic platinum coordination complex is selected from the group consisting of cisplatin, carboplatin, tetraplatin, ormiplatin, iproplatin and oxaliplatin.

8. A composition in accordance with claim 1, wherein said antineoplastic platinum coordination complex is cisplatin and said compound is selected from the group consisting of:

12. A method in accordance with claim 10, wherein said antineoplastic platinum coordination complex is selected from the group consisting of cisplatin, carboplatin, tetraplatin, ormiplatin, iproplatin and oxaliplatin; and said compound is selected from the group consisting of
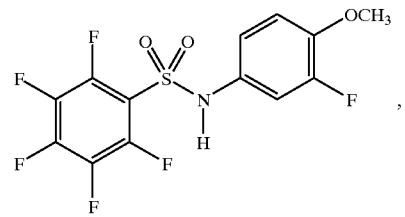
,
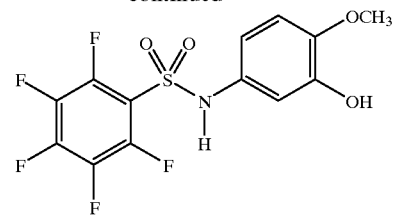
,
and
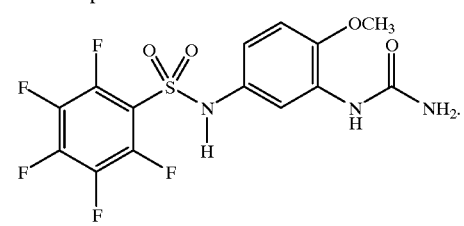
.
* * * * *